United States Patent [19]

Hoch et al.

[11] 4,038,309
[45] July 26, 1977

[54] PRODUCTION OF 2-HYDROXYNAPHTHALENE-3-CARBOXYLIC ACID

[75] Inventors: Helmut Hoch; Hans-Juergen Quadbeck-Seeger, both of Ludwigshafen, Germany

[73] Assignee: BASF Aktiengesellschaft, Ludwigshafen, Germany

[21] Appl. No.: 643,524

[22] Filed: Dec. 22, 1975

Related U.S. Application Data

[62] Division of Ser. No. 422,547, Dec. 6, 1973, abandoned.

[30] Foreign Application Priority Data

Feb. 12, 1972    Germany ................. 2260637

[51] Int. Cl.$^2$ ................................ C07C 51/15
[52] U.S. Cl. ................................... 260/520 A
[58] Field of Search ..................... 260/520 A

[56] References Cited

U.S. PATENT DOCUMENTS

| | | | |
|---|---|---|---|
| 1,470,039 | 10/1923 | Wallach | 260/520 A |
| 1,503,984 | 8/1924 | Cone | 260/520 A |
| 2,132,356 | 10/1938 | Lecher et al. | 260/520 A |
| 2,132,357 | 10/1938 | Lecher et al. | 260/520 A |
| 2,193,336 | 3/1940 | Lecher et al. | 260/520 A |
| 2,453,105 | 11/1948 | Wotthuis et al. | 260/520 A |
| 2,534,022 | 12/1950 | Higgens | 260/520 A |
| 2,544,881 | 3/1951 | Hodges et al. | 260/520 A |
| 2,685,600 | 8/1954 | Morris et al. | 260/520 A |
| 2,807,643 | 9/1957 | Hartley | 260/520 A |
| 2,824,129 | 2/1958 | Nordt et al. | 260/520 A |
| 2,824,892 | 2/1958 | Barkley | 260/520 A |
| 3,405,169 | 10/1968 | Levy et al. | 260/520 A |
| 3,405,170 | 10/1968 | Levy et al. | 260/520 A |
| 3,655,744 | 4/1972 | Yashuhara et al. | 260/520 A |

OTHER PUBLICATIONS

Lecher et al., "J. Prakt. Chem.," 4th Ser., 3, 232(1956).
Serdel et al., "J. Prakt. Chem.," 4th Ser., 2, 53(1955).

*Primary Examiner*—Norman Morgenstern
*Attorney, Agent, or Firm*—Keil, Thompson & Shurtleff

[57] ABSTRACT

The production of 2-hydroxynaphthalene-3-carboxylic acid by heating sodium β-naphtholate in the presence of an araliphatic compound containing two aromatic radicals and/or in the presence of an aromatic ether having at least one aromatic radical etherified with an aliphatic, cycloaliphatic or araliphatic radical at a temperature of at least 200° C, reaction with carbon dioxide and reaction of the salt formed with acid. The resultant 2-hydroxy-naphthalene-3-carboxylic acid is a starting material for the production of dyes, a coupling component of surface coating colors and chrome dyes and also a developer for diazotizable dyes.

18 Claims, No Drawings

PRODUCTION OF 2-HYDROXYNAPHTHALENE-3-CARBOXYLIC ACID

RELATED APPLICATION

This application is a division of our copending application Ser. No. 422,547, filed Dec. 6, 1973 now abandoned.

The invention relates to a process for the production of 2-hydroxynaphthalene-3-carboxylic acid by heating sodium $\beta$-naphtholate in the presence of an araliphatic compound containing two aromatic radicals and/or in the presence of an aromatic ether having at least one aromatic radical etherified with an aliphatic, cycloaliphatic or araliphatic radical at a temperature of at least 200° C, reaction with carbon dioxide and reaction of the salt formed with acid.

The process known for a long time for making 2-hydroxynaphthalene-3-carboxylic acid from $\beta$-naphthol consists in converting $\beta$-naphthol into a sodium salt by reaction with caustic soda solution and then converting the sodium salt into the disodium salt of 2-hydroxynaphthalene-3-carboxylic acid with carbon dioxide at elevated temperature and superatmospheric pressure (BIOS Report No. 986, pages 234 et seq.; Ullmanns Encyclopadie der technischen Chemie, volume 12, pages 606 et seq.). This method is unsatisfactory because it requires special apparatus and involves high operating and energy costs. One main difficulty consists in the rapid and complete dehydration of the sodium $\beta$-naphtholate prior to the carboxylation reaction. Even a small amount of water present in the carboxylation reaction will reduce the yield of disodium salt of 2-hydroxynaphthalene-3-carboxylic acid. Drying sodium $\beta$-naphtholate is difficult and protracted. Since transfer of heat is unfavorable in the solid $\beta$-naphtholate local overheating of the solid salt resulting in its decomposition may occur even when the heating is carefully controlled, a procedure which takes a long time and consequently is costly.

Modified methods have been devised to improve procedure: U.S. Pat. No. 2,132,357 discloses the reaction of the sodium naphtholate in the presence of pyridine and its homologs. Nickel has to be used as the material of construction because iron vessels are corroded and the iron compounds thus formed appreciably promote the formation of naphthoxanthone as a byproduct. The patent specification states that good solubility of carbon dioxide in the solvent used is an important condition of rapid carboxylation. Odor nuisance and the toxicity of the solvent are disadvantages in this method when it is operated on an industrial scale. When the naphtholate is distilled a large part of the solvent passes over in an azeotropic mixture with water and is thus lost to the reaction. It is difficult and expensive to recover the solvent; residues thereof remaining in the waste water pose problems in relation to the environment.

U.S. Pat. No. 2,132,356 discloses the use of cyclic ethers such as dioxane as solvents for the reaction. As in the case of pyridine, iron cannot be used as the material of construction. The ether used is also for the most part removed from the reaction and this involves the difficulties in processing mentioned above. A high pressure has to be used for the reaction. Since dioxane and its derivatives may contain peroxide as a byproduct there are problems in relation to safety in operation.

U.S. Pat. No. 1,503,984 discloses the use of paraffin wax and paraffin oil as the reaction medium; these substances retard the reaction and are difficult to recover. The method is troublesome and uneconomical on an industrial scale. Dialkyl ketones are used in the method described in British Pat. No. 638,196. Large amounts of solvent have to be used to obtain solution and this entails high costs of materials and follow space-time yield.

German Laid-Open Specification (DOS No. 2,132,296 discloses the use of diphenyl, diphenyl oxide or an alkylnaphthalene having alkyl groups of one to four carbon atoms as the reaction medium. The solvents are volatile in steam and the abovementioned difficulties regarding processing, recovery of solvent and disposal of waste water are also encountered. Alkylnaphthalenes are difficultly accessible as compared with the other solvents and are comparatively uneconomical compounds.

The object of the invention is to provide a new process for producing 2-hydroxynaphthalene-3-carboxylic acid in good yields and purity by a simple and economical method.

We have found that 2-hydroxynaphthalene-3-carboxylic acid is obtained advantageously by reaction of sodium $\beta$-naphtholate in an organic solvent with carbon dioxide at elevated temperature by (a) heating the sodium naphtholate in a first stage in the presence of an araliphatic compound containing at least two aromatic radicals combined with one another by way of a cycloaliphatic and/or araliphatic radical and/or an aromatic ether in which at least one aromatic radical is combined with at least one aliphatic, cycloaliphatic and/or araliphatic radical by way of an oxygen atom to a temperature of at least 180° C, (b) reacting it in a second stage with carbon dioxide at a temperature of at least 180° C and (c) converting the salt of 2-hydroxynaphthalene-3-carboxylic acid thus formed into 2-hydroxynaphthalene-3-carboxylic acid by adding an acid.

The reaction may be represented by the following equations:

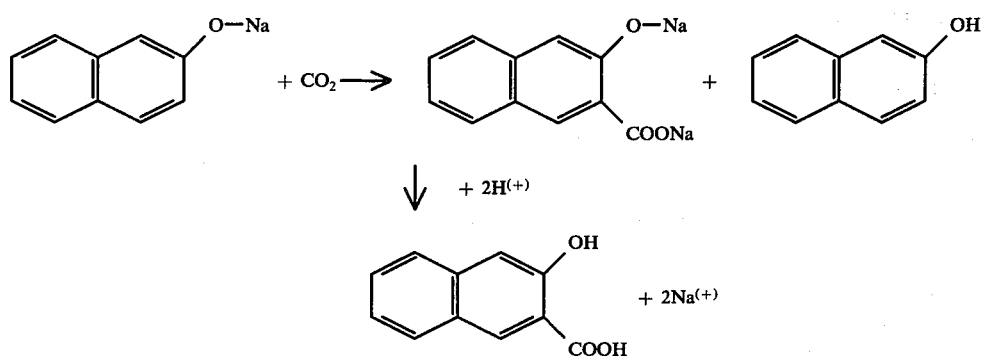

The process of the invention gives 2-hydroxynaphthalene-3-carboxylic acid in a good yield and purity in a simpler and more economical manner than prior art methods. The araliphatic compounds of the invention are usually obtained as byproducts from other syntheses, for example polymerization and oligomerization of styrene and its derivatives, or are readily accessible by Friedel-Crafts syntheses with benzyl chlorides and naphthalenemethyl chlorides and benzene, benzene derivatives or diphenylmethane and its homologs; for example dibenzylbenzenes and mixtures of their isomers prepared by the process disclosed in German Pat. No. 1,085,877 may be used. Aromatic ethers for the purposes of the invention are easily accessible by reaction of alkali metal phenolates and alkyl or aralkyl halides or the corresponding sulfates. Contrasted with the use of cyclic ethers such as dioxane as solvents for the reaction, the very good solvent power for sodium β-naphtholate when the ethers according to the invention are used is surprising in that it permits a high concentration of sodium β-naphtholate in the solvent. Since the araliphatic compounds and aromatic ethers according to the invention have little or no volatility in steam, it is an advantage that only water is removed upon heating while the naphtholate remains in the solvent. Difficulties in relation to recovery of the araliphatic compounds and aromatic ethers and pollution problems are therefore negligible. Iron may be used as material of construction without corrosion and/or increased formation of byproducts being observed to any significant extent. The plant is safe and simple to operate on an industrial scale. All these advantageous results are surprising having regard to the prior art. It would have been expected that the fairly high molecular weight and bulky structure of the araliphatic compounds and aromatic ethers would have little or no solubility for carbon dioxide and/or the naphtholate and would thus have a retarding effect on the rate and yield of the reaction. Since according to the statements in German Laid-Open Specification (DOS) No. 2,132,296 at the bottom of page 8 naphthalene gives poorer yields of end product than alkylnaphthalenes it would have been supposed that in the case of araliphatic compounds with a plurality of aromatic nuclei and/or without terminal alkyl groups or in the case of aromatic ethers having a plurality of aromatic nuclei and/or a plurality of aralkoxy groups the results would have been poorer.

The araliphatic compounds and aromatic ethers serve as the reaction medium, wholly or partly dissolve the naphtholate and are solvents or suspension agents for the reaction mixture. It is advantageous to use as the reaction medium an aralkyl compound which contains two, three or four benzene and/or naphthalene nuclei which are not fused, the nuclei preferably being connected to one another by way of cyclohexylene groups, cyclopentylene groups and/or alkylene groups of one to eight and particularly one to four carbon atoms. In the case of cycloaliphatic compounds having two nuclei it is advantageous for one nucleus to be fused with the cycloaliphatic radical but for the other nucleus not to be fused.

A cycloaliphatic radical, for example cyclohexylene or cyclopentylene, which connects two aromatic radicals may bear substituents, for example alkyl groups, one aromatic radical being fused with the cycloaliphatic radical and the other aromatic radical being combined direct with a carbon atom of the cycloaliphatic radical. Preferred compounds include those having the formula.

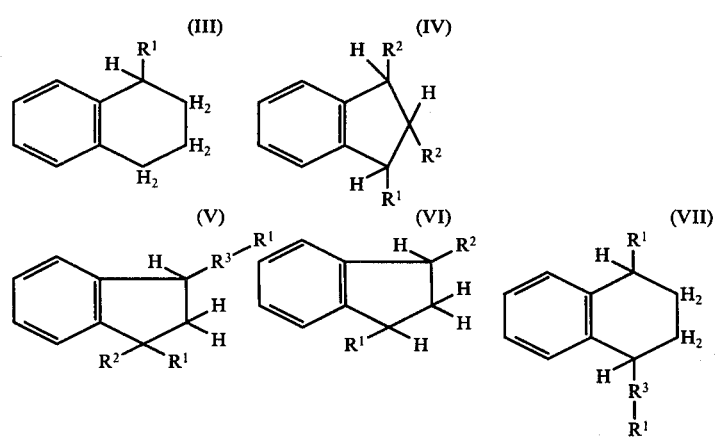

in which $R^1$ as aryl and particularly phenyl or naphthyl, $R^2$ is alkyl, advantageously of one to three carbon atoms or hydrogen, $R^3$ is alkylene of one to eight carbon atoms and particularly of one to three carbon atoms. Alkyl or alkylene may be linear or branched. The above radicals may bear groups which are inert under the reaction conditions, for example alkyl of one to three carbon atoms, as substituents.

Examples of suitable solvents or suspension agents are: napthyltetrahydronaphthalene, phenyltetrahydronaphthalene, 1-phenyl-4-phenylbutyltetrahydronaphthalene, 1-phenyl-4-naphthylethyltetrahydronaphthalene, 1-phenyl-2,3-dimethylindan, 1-phenylethyl-3-phenyl-3-methylindan.

Dimers and oligomers of styrene and particularly 1-methyl-3-phenylindan and 1-phenyl-4-phenylethyltetrahydronaphthalene are especially preferred. These are secondary products of styrene some of which can be isolated from the bottoms of styrene distillation and some in the dimerization of styrene into 1-methyl-3-phenylindan by distillation. The distillation bottoms may also be used direct for the reaction according to the invention, conveniently after hydrogenation of the olefins such as 1,3-diphenylbutene, 1,3-diphenylbutene, 1,3-diphenylhexene, or methylstilbene. Other arylalkylbenzenes may be prepared by oligomerization of styrene. 1-methyl-3-phenylindan and 1-phenyl-4-phenylethyltetrahydronaphthalene in the pure form and in the form of the said industrial mixtures dissolve surprisingly large amounts of sodium $\beta$-naphtholate. The solvent power is up to 80% by weight of sodium $\beta$-naphtholate at from 250° to 260° C.

Advantageous aromatic ethers contain two, three or four benzene and/or naphthalene nuclei which are not fused with one another and with which there may be combined in each case one, two, or three aralkyl radicals, cycloalkyl radicals and/or alkyl radicals, preferably alkyl radicals, by way of an oxygen atom, so that in all at least one of the said radicals is combined with one of the said nuclei by way of an oxygen atom, and which moreover may be combined with one another by way of alkylene or a radical-O-R-O- in which R is alkylene or aralkylene. Preferred aromatic ethers are those of the formula:

A. Aromatic ethers with one naphthyl group

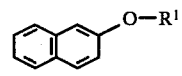
(IIIa)

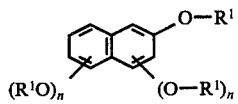
(IVa)

B. Aromatic ethers having two naphthyl groups

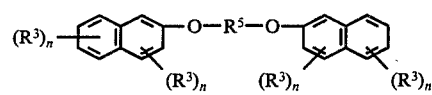
(Va)

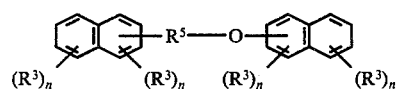
(VIa)

-continued

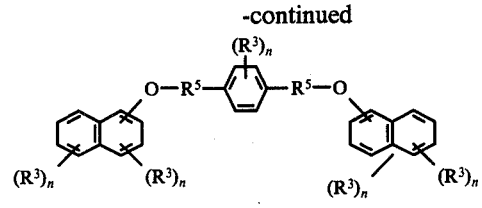
(XI)

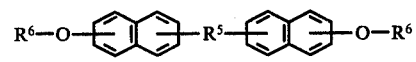

C. Aromatic ethers having two or more phenyl groups

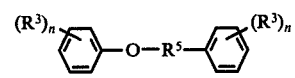
(VIIa)

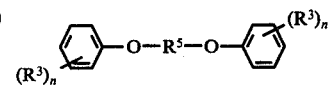
(VIIIa)

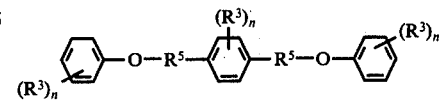
(X)

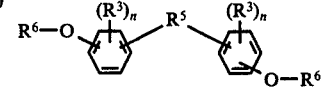
(XII)

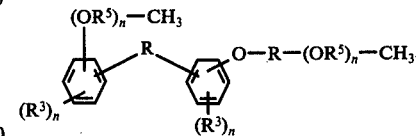
(XIII)

in which $R^1$ is alkyl of one to four carbon atoms, cyclopentyl, cyclohexyl, $-R^5-(OR^5)_n-CH_3$,

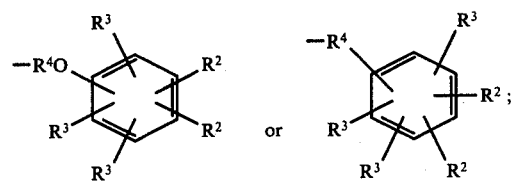

individual radicals $R^2$ and $R^3$ may be identical or different and each is alkyl or alkoxy in each case of one to four carbon atoms, cycloalkyl or cycloalkoxy of five or six carbon atoms, hydrogen or $-(OR^5)_n-CH_3$; one radical $R^2$ may also be

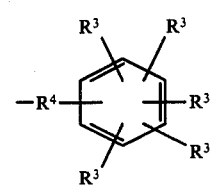

or two radicals $R^2$ may together be

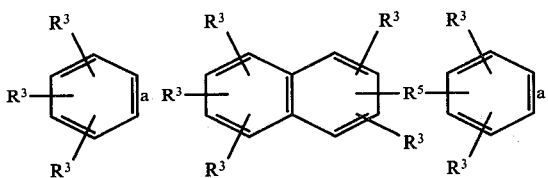

fused with the benzene nucleus at the side $a$ in which $R^3$ has the above meanings, $R^4$ is alkylene of two to four carbon atoms or

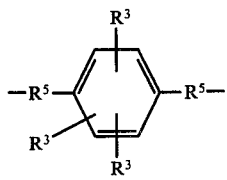

in which $R^3$ has the above meanings, $R^5$ is alkylene of two to four carbon atoms, $R^6$ is alkyl of one to four carbon atoms and $n$ is zero, 1, 2 or 3. The said alkyl and alkylene radicals may be linear or branched. The said radicals may also bear groups which are inert under the reaction conditions, for example alkoxy or alkyl groups, in each case of one to three carbon atoms, as substituents.

Examples of suitable solvents (suspension agents) are α-naphthol methyl ether, β-naphthol methyl ether, β-naphthol ethyl ether, β-naphthol propyl ether, ethylene glycol diphenyl ether, 1,2-dinaphthoxybutane, 1,2-dinaphthoxyethane, 1,3-diphenyoxypropane, 1,4-diphenoxybutane, 1,5-diphenoxypentane, 1,2-diphenoxypropane, 1,3-diphenoxybutane, phenoxy-(γ-phenylpropyl) ether, 2'-methoxyphenylethyl phenyl ether, naphthyl-(2) propylphenyl ether, 1,3-di-(2'-methyl)-phenoxypropane, 1,4-di-(3'-methyl)-phenoxybutane, 1,2-di-(2'-methyl)-phenoxyethane, 1,2-di-(3'-methyl)-phenoxyethane, 1,2-di-(4'-methyl)-phenoxyethane, 1,2-di-(2'-methyl)phenoxypropane, 1,2-di-(3'-methyl)-phenoxypropane, 1,2-di-(4'-methyl)-phenoxypropane, ω,ω'-diphenoxy-1,4-diethylenebenzene, 2,4,5,8-tetramethoxynaphthalene, 4,5,8-triethyl-β-naphthol methyl ether, β-naphthol cyclohexyl ether, α-naphthol(-monobutoxy)-triethylene glycol ether, ω,ω'-di-naphthoxy-(2',2'')-1,4-diethylenebenzene, 1,4-bis-(5'-methoxynaphthyl)butane, 4,4'-dimethoxy-2,2'-dimethyldiphenylethane, and 1,3-diphenylpropane-4',4''-bis-(ω,ω'-ethoxydiethyleneglycol) ether.

Readily accessible ethers of β-naphthol are specially preferred and particularly β-naphthol methyl ether and the reaction products of alkali metal naphtholates, alkali metal phenolates or alkali metal cresolates, for example sodium naphtholates, sodium phenolates or sodium cresolates with ω-dihalogen compounds and particularly with the easily accessible 1,2-dichloroethane and 1,2-dichloropropane and 1,4-dibromobutane. The aromatic ethers in pure form or in the form of technical mixtures will dissolve surprisingly large amounts of sodium β-naphtholate. Their solvent power for sodium β-naphtholate is up to 80% by weight at 250° to 260° C.

The reaction may be carried out with one or more than one aromatic ether or with one or more than one araliphatic compound as the reaction medium. As a rule araliphatic compounds are used which have a boiling point of at least 200° C, advantageously from 270° to 400° C and preferably from 270° to 350° C an in an amount of from 20 to 100% and preferably from 25 to 30% by weight based on naphtholate, or aromatic ethers are used with a boiling point of at least 200° C, advantageously from 250° to 400° C and preferably from 270° to 350° C and in an amount of from 20 to 100% and preferably from 25 to 30% by weight based on naphtholate. The naphtholate may be used as a pure substance; it is convenient however to combine the production of the naphtholate and the first stage of the process of the invention and thus to carry out a three-stage process in one vessel, preferably with all stages in the presence of the araliphatic compound or the aromatic ether. The naphtholate may be prepared according to one of the known manufacturing methods for naphthol using sodium compounds such as sodium carbonate or sodium hydroxide to form the salt (Ullmanns Encyklopadie der technischen Chemie, volume 12, pages 603 and 604) conveniently direct from the melt in which it has been prepared from sodium naphthalene-β-sulfonate by fusion with caustic soda solution, by extraction. Extraction is advantageously carried out with intense stirring of the melt with an araliphatic compound or appropriate mixture at at least 230° C and conveniently from 240° to 275° C, and undissolved sodium sulfite and excess caustic soda are separated by filtration. The solution or suspension of sodium-β-naphtholate obtained in this way is if desired heated and used immediately for the carboxylation reaction. The araliphatic compound or aromatic ether may be used in the relative proportions with relation to the naphtholate specified above. If the sodium-β-naphtholate is extracted from the alkaline melt of the sodium salt of naphthalene-β-sulfonic acid, an amount of from 30 to 100% and preferably of 30 to 50% by weight of araliphatic compound is chosen based on naphtholate. Production of the naphtholate may be carried out at atmospheric or superatmospheric pressure, continuously or batchwise. The mixture from the naphtholate production supplied to the first stage of the reaction of the invention advantageously contains a total amount of sodium calculated as sodium hydroxide which is the stoichiometric amount based on the total naphthol in the mixture. If desired an excess beyond the stoichiometric amount of for example up to 20% by weight of naphthol may be present based on the total amount of sodium calculated as sodium hydroxide in the original mixture. It is also possible to heat to the reaction temperature a mixture of β-naphthol, araliphatic compound or aromatic ether and aqueous caustic soda solution, with or without an inert gas such as nitrogen.

In the first stage of the reaction the starting mixture is heated to a temperature of at least 180° C, preferably from 200° to 280° C and particularly from 240° to 265° C, at atmospheric or superatmospheric pressure, continuously or batchwise. The second stage of the reaction (carboxylation) is carried out continuously or batchwise under the same conditions of temperature and pressure. When the starting mixture is heated, for example for thirty minutes to one hour, water distils over. The carboxylation is conveniently carried out at superatmospheric pressure, for example of 2 to 50 atmospheres and particularly from 3 to 10 atmospheres, and with an amount of carbon dioxide of from 0.5 to 10 moles and preferably from 0.5 mole to 2 moles, based on naphtholate. The reaction period for the carboxylation is conveniently from one to four hours. The end product is then isolated by a conventional method. For example the mixture may be cooled and the suspension of the disodium salt of 2-hydroxy-3-naphthalene carboxylic acid introduced into water or when an araliphatic compound or aromatic ether having a boiling point similar to that of β-naphthol is used the araliphatic compound or the aromatic ether and the whole of the β-naphthol may be distilled off in vacuo and the residue dissolved in water at from about 90° to 100° C. When for example a trimer of styrene or of 1,4-diphenoxybutane is used the β-naphthol formed may be distilled off in vacuo after the end of the carboxylation reaction and the remaining suspension of the disodium salt of 2-hydroxynaphthalene-3-carboxylic acid may be stirred with water or poured into water.

Acid is then added to the aqueous mixture in order to obtain the free carboxylic acid; any acid and method of converting a salt into the corresponding acid may be used within a wide range. The pH of the aqueous mixture which contains the disodium salt of 2-hydroxynaphthalene-3-carboxylic acid together with small amounts of sodium β-naphtholate is adjusted to about 5° to 60° to 70° C with aqueous hydrochloric acid (for example from 5 to 35% strength), β-naphthol liberated is extracted by an araliphatic compound or an aromatic ether as solvent and then the organic phase is separated from the aqueous phase. The β-naphthol precipitated after acidification of the aqueous phase to a pH of about 5 may also for example be filtered through a filter press. The aqueous phase freed from β-naphthol by extraction or filtration is then conveniently acidified at 85° to 95° C with aqueous hydrochloric acid (for example from 5 to 35% by weight strength) to pH about 3, stirred for 5 to 15 minutes, cooled to 50° C and suction filtered.

2-hydroxynaphthalene-3-carboxylic acid prepared by the process of the invention is a valuable starting material for the production of dyes and is a coupling component of surface coating colors and chrome dyes and also a developer for diazotizable dyes. The above-mentioned publications, particularly the standard work of Ullmann, volume 12, page 609 may be referred to as regards use of the product.

The following Examples illustrate the invention. The parts specified are by weight.

EXAMPLE 1

A stirred autoclave is charged with 1500 parts of β-naphthol, 770 parts of caustic soda solution (50% by weight strength) and 460 parts of 1-methyl-3-phenylindan. The mixture is mixed well under nitrogen, heated to an internal temperature of 260° C and kept at this temperature for thirty minutes. Dehydration is then practically complete. Carboxylation is effected in an autoclave at a temperature of 260° C with dry carbon dioxide at a pressure of 7 atmospheres. The absorption of carbon dioxide (180 parts in all) is monitored by way of a gas meter. After the absorption is complete β-naphthol and 1-methyl-3-phenylindan are distilled off together by applying a vacuum of 20 mm. The autoclave is then cooled and the reaction mixture is stirred with water at 95° C.

The remainder of the organic phase is separated from the aqueous phase at a temperature of 75° C and then the aqueous phase is acidified with hydrochloric acid to pH about 6 while stirring vigorously. β-naphthol thus deposited is cooled to 30° C and suction filtered, and the clear aqueous mother liquor is acidified to a pH of 3 with hydrochloric acid (35% by weight strength) at a temperature of 85° to 90° C and stirred for another 10 minutes. After the mixture has been cooled to 50° C the crystals of 2-hydroxynaphthalene-3-carboxylic acid formed are suction filtered and dried in vacuo at 70° C. 688 parts of end product is obtained with a melting point of 215° to 219° C. This is 76% of theory based on β-naphthol used up.

EXAMPLE 2

A stirred autoclave is charged with 1525 parts of '-naphthol, 770 parts of caustic soda solution (50% by weight strength) and 500 parts of 1-phenyl-4-phenylethyltetrahydronaphthalene. In the manner described in Example 1 the autoclave is heated to an internal temperature of 260° C while stirring and kept at this temperature for ten minutes. Residual moisture is removed from the autoclave for five minutes at a pressure of 40 mm. Dehydration is practically complete and water is collected as distillate. Carbon dioxide is then introduced into the autoclave at the internal temperature of 260° C until a pressure of 7 atmospheres has been reached. Carboxylation and the following processing are carried out as described in Example 1. The mixture of organic phase and aqueous phase is acidified to a pH of about 5 at a temperature of 75° C with vigorous stirring, so that the liberated β-naphthol is taken up by the solvent. The organic phase is separated from the aqueous layer. The clear aqueous phase is heated to 85° to 90° C, acidified to pH about 3 with hydrochloric acid and stirred for another ten minutes. After cooling to 50° C the yellowish crystals of 2-hydroxynaphthalene-3-caboxylic acid are suction filtered and dried in vacuo at 70° C. 705 parts of 2-hydroxynaphthalene-3-carboxylic acid having a melting point of 214° to 217° C is obtained (78% of theory based on β-naphthol used up).

EXAMPLE 3

204 parts of technical sodium β-naphtholate melt containing 100 parts of sodium- β-naphtholate and 100 parts of sodium sulfite is stirred at 250° to 260° C with 150 parts of methylphenylindan for fifteen minutes. The undissolved sodium sulfite is allowed to settle and the hot solution of sodium β-naphtholate in methylphenylindan at 260° C is pumped into a stirred autoclave which has been preheated to 255° C. The autoclave is closed and at an internal temperature of 255° C dry carbon dioxide is pressed in up to a pressure of 5 atmospheres. Carboxylation and processing are carried out analogously to Example 1. 34 parts of 2-hydroxynaphthalene-3-carboxylic acid having a melting point of 212° to 215° C is obtained (60% of theory based on β-naphthol used up).

EXAMPLE 4

A stirred autoclave is charged with 1220 parts of β-naphthol, 620 parts of caustic soda solution (50% by weight strength) and 360 parts of β-naphthol methyl ether. The mixture is mixed well under nitrogen, heated to an internal temperature of 260° C and kept at this temperature for thirty minutes. Carboxylation is carried out in an autoclave at a temperature of 260° C with dry carbon dioxide at a pressure of 7 atmospheres. The absorption of carbon dioxide (a total of 145 parts) is monitored by way of a gas meter. When the absorption is complete β-naphthol and β-naphtol methyl ether are distilled off together by applying a vacuum of 20 mm. The autoclave is then cooled and the reaction mixture is stirred with water at 95° C. The rest of the organic phase is then separated from the aqueous phase at the said temperature and the aqueous phase is acidified to pH about 6 with hydrochloric acid with vigorous stirring.

The β-naphthol thus separated is suction filtered after cooling to 30° C, the clear aqueous mother liquor is acidified to pH 3 with hydrochloric acid (35% by weight strength) at a temperature of 85° to 90° C and stirred for another ten minutes. After the mixture has been cooled to 50° C the crystals of 2-hydroxynaphthalene-3-carboxylic acid formed are suction filtered and dried in vacuo at 70° C. 545 parts of end product (75% of theory based on reacted β-naphthol) is obtained with a melting point of 215° to 219° C.

EXAMPLE 5

A stirred autoclave is charged with 1220 parts of β-naphthol, 620 parts of caustic soda solution of 50% by weight strength and 360 parts of 1,4-diphenoxybutane. As described in Example 4 the autoclave is heated to an internal temperature of 260° C while stirring and kept at this temperature for ten minutes. Residual moisture is removed from the autoclave for five minutes at a pressure of 40 mm. Dehydration is practically complete. Carbon dioxide is then passed into the autoclave at the internal temperature of 260° C up to a pressure of 7 atmospheres. Carboxylation followed by processing are carried out analogously to Example 4. The mixture of organic phase and aqueous phase is acidified to pH about 5 at a temperature of 95° C with vigorous stirring so that the β-naphthol liberated is taken up by the solvent. The organic phase is separated from the aqueous layer. The clear aqueous phase is heated to 85° to 90° C, acidified with hydrochloric acid to pH about 3 and stirred for another 10 minutes. After cooling to 50° C the yellowish crystals of 2-hydroxynaphthalene-3-carboxylic acid are suction filtered and dried in vacuo at 70° C. 560 parts of 2-hydroxynaphthalene-3-carboxylic acid (77% of theory based on β-naphthol reacted) is obtained with a melting point of 214° to 217° C.

EXAMPLE 6

A stirred autoclave is charged with 1220 parts of β-naphthol, 620 parts of caustic soda solution (50% by weight strength) and 360 parts of 1,2-diphenoxyethane. The mixture is heated while stirring to an internal temperature of 260° C and kept at this temperature for ten minutes as in Example 4. Residual moisture is removed from the autoclave within five minutes at 100 mm pressure; dehydration is practically complete. Carbon dioxide is then passed into the autoclave at an internal temperature of 260° C up to a pressure of 7 atmospheres. Carboxylation followed by processing are carried out as in Example 4. The mixture of organic phase and aqueous phase is acidified to about pH 5 at a temperature of 95° C with vigorous stirring and the β-naphthol liberated is separated with the organic phase. The clear aqueous phase is heated to 85° to 90° C, acidified to pH about 3 with hydrochloric acid and stirred for another thirty minutes. After cooling to 50° C the yellowish crystals of 2-hydroxy-naphthalene-b 3-carboxylic acid are suction filtered and dried at 70° C in vacuo. 550 parts (75.5% of theory based on reacted β-naphthol) of 2-hydroxynaphthalene-3-carboxylic acid is obtained with a melting point of 214° to 216° C.

EXAMPLE 7

A stirred autoclave is charged with 1200 parts of β-naphthol, 620 parts of caustic soda solution (50% by weight strength) and 320 parts of 1,2-di-(3'-methyl)-phenoxyethane. As described in Example 4 the mixture is heated to an internal temperature of 260° C while stirring and kept at this temperature for ten minutes. Residual moisture is removed from the autoclave at 100 mm pressure during five minutes; dehydration is practically complete. Carbon dioxide is then passed into the autoclave at the internal temperature of 260° C up to a pressure of 7 atmospheres. After absorption of carbon dioxide has ended the β-naphthol formed during the reaction is distilled off in vacuo. Further processing is carried out as in Example 5. 545 parts of 2-hydroxynaphthalene-3-carboxylic acid (75% of theory based on β-naphthol reacted) is obtained with a melting point of 214° to 217° C.

EXAMPLE 8

A stirred autoclave is charged with 1210 parts of β-naphthol, 620 parts of caustic soda solution (50% by weight strength) and 300 parts of 1,2-dinaphthoxyethane. As described in Example 4 the mixture is heated to an internal temperature of 260° C while stirring and kept at this temperature for ten minutes. During this period the residual moisture is removed from the autoclave by applying 100 mm pressure. Dehydration is practically complete. Carbon dioxide is then introduced at the internal temperature of 260° C up to a pressure of 7 atmospheres. After the absorption of carbon dioxide is completed the β-naphthol formed in the reaction is distilled off in vacuo. Further processing is carried out as in Example 5. 525 parts (72% of theory based on reacted β-naphthol) of 2-hydroxy-naphthalene-3-carboxylic acid is obtained with a melting point of 212° to 215° C.

EXAMPLE 9

A stirred autoclave is charged with 1220 parts of β-naphthol, 620 parts of caustic soda solution (50% by weight strength) and 300 parts of ω,ω'-diphenoxy-1,4-diethylenebenzene. The mixture is heated while stirring to an internal temperature of 260° C and kept at this temperature for 10 minutes as described in Example 4. During this period the residual moisture is removed from the autoclave by applying a pressure of 100 mm. Dehydration is practically complete. Carboxylation and processing of the reaction mixture are carried out analogously to Example 5. 545 parts (75% of theory based on reacted β-napthol) of 2-hydroxynaphthalene-3-carboxylic acid is obtained with a melting point of 214° to 217° C.

EXAMPLE 10

A stirred autoclave is charged with 1210 parts of β-naphthol, 620 parts of caustic soda solution (50% by weight strength) and 280 parts of 4,4'-dimethoxydiphenylethane. Dehydration and carboxylation are carried out as in Example 4. After absorption of carbon dioxide has been completed the autoclave is cooled and the reaction mixture is stirred with water at 95° C. The organic phase and the β-naphthol formed in the reaction are then separated from the aqueous phase at this temperature. The aqueous phase is acidified to pH about 6 with hydrochloric acid to liberate unreacted β-naphthol which is suction filtered after the mixture has been cooled to 30° C. The 2-hydroxynaphthalene-3-carboxylic acid is liberated from the clear filtrate by acidification with hydrochloric acid (35% by weight strength) to a pH of about 3 at a temperature of 85° to 90° C, filtered at 50° C and dried in vacuo at 70° C. 540 parts (74% of theory based on β-naphthol reacted) of 2-hyroxynaphthalene-3-carboxylic acid is obtained with a melting point of 212° to 215° C.

We claim:

1. A process for the production of 2-hydroxynaphthalene-3-carboxylic acid which comprises heating sodium β-naphtholate in a first stage to a temperature of at least 180° C as a solution of suspension in a liquid araliphatic compound having one of the formulae

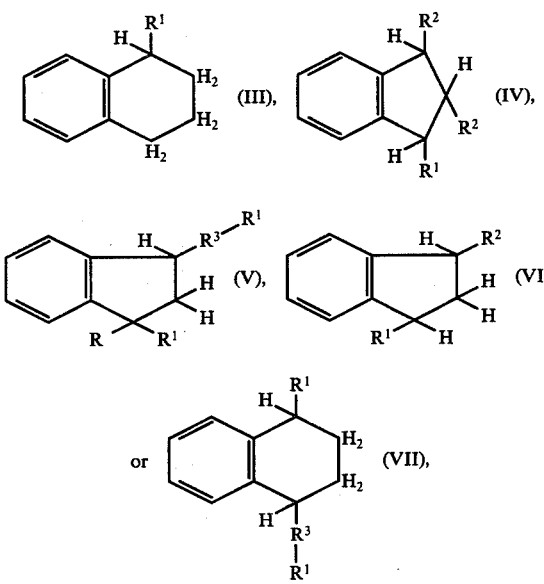

in which R¹ is phenyl or naphthyl, R² is alkyl of one to four carbon atoms or hydrogen, R³ is alkylene of one to eight carbon atoms, and the phenylene groups of the compounds of formulae III through VII optionally bearing alkyl of one to three carbon atoms as substituents thereof, then reacting sodium naphtholate after heating thereof in said first stage with carbon dioxide in a second stage at a temperature of at least 180° C to form the sodium salt of 2-hydroxynaphthalene-3-carboxylic acid, and acidifying the latter compound to convert it into 2-hydroxy-naphthalene-3-carboxylic acid.

2. A process as set forth in claim 1 where said araliphatic compound is employed in an amount of 20 to 100% by weight based on said naphtholate.

3. A process as set forth in claim 1 wherein the reaction in the second stage conducted at a temperature in the range of 200° to 280° C.

4. A process as set forth in claim 3 wherein the reaction in the second stage is conducted at a pressure in the range of from 2 to 50 atmospheres and an amount of carbon dioxide in the range of from 0.5 mole to 10 moles, based on said naphtholate.

5. A process as set forth in claim 1 wherein said araliphatic compound is 1-methyl-3-phenylindan or 1-phenyl-4-phenylethyltetrahydronaphthalene.

6. A process for the production of 2-hydroxynaphthalene-3-carboxylic acid which comprises heating sodium β-naphtholate in a first stage to a temperature of at least 180° C as a solution or suspension in an aromatic ether having one of the formulae (IIIa)

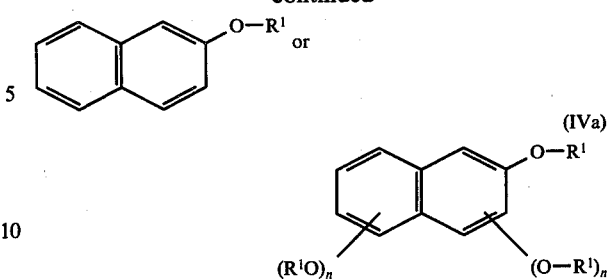

(IVa)

in which R¹ is alkyl of one to four carbon atoms, cyclopentyl, cyclonexyl, —R⁵—(OR⁵)$_n$—CH₃,

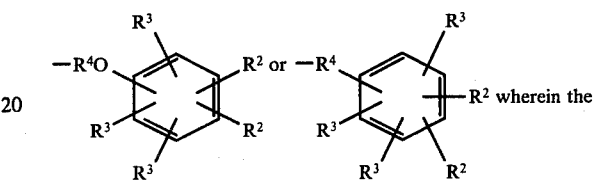

individual radicals R² and R³ may be identical or different and each is alkyl or alkoxy in each case of one to four carbon atoms, cycloalkyl or cycloalkoxy of five or six carbon atoms, hydrogen or —(OR⁵)$_n$—CH₃, one radical R² may also be:

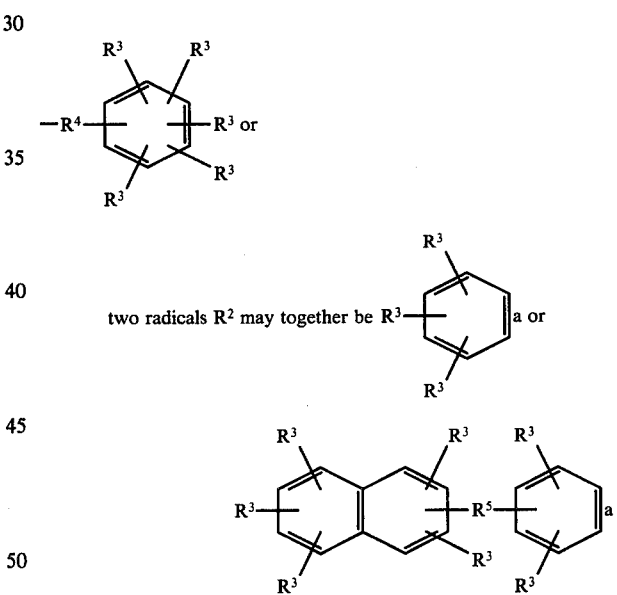

fused with the benzene nucleus at the side a in which R³ has the above meanings, R⁴ is alkylene of two to four carbon atoms or

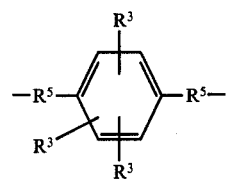

in which R³ has the above meaning, R⁵ is alkylene of two to four carbon atoms, R⁶ is alkyl of one to four carbon atoms and n is zero, 1, 2 or 3 and the said radicals may bear groups which are inert under the reaction conditions for example alkoxy or alkyl of one to three carbon atoms in each case as substituents, reacting the sodium naphtholate from said first stage with carbon dioxide in a second stage at a temperature of at least 180° C, and acidifying the sodium salts of 2-hydroxynaphthalene-3-carboxylic acid to convert it to 2-hydroxynaphthalene-3-carboxylic acid.

7. A process as set forth in claim 6 wherein the amount of the aromatic ether employed is in the range of 20 to 100% by weight based on said naphtholate.

8. A process as set forth in claim 6 wherein the carboxylation in the second stage is conducted at a pressure in the range of from 2 to 50 atmospheres and with an amount of carbon dioxide in the range of from 0.5 mole to 10 moles, based on said naphtholate.

9. A process as set forth in claim 6 wherein said aromatic ether is β-naphthol methyl ether.

10. A process for the production of 2-hydroxynaphthalene-3-carboxylic acid which comprises heating sodium β-naphtholate in a first stage to a temperature of at least 180° C as a solution or suspension in an aromatic ether having one of the formulae

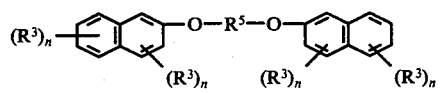
(Va)

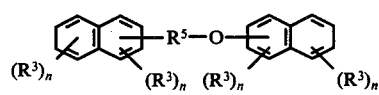
(VIa)

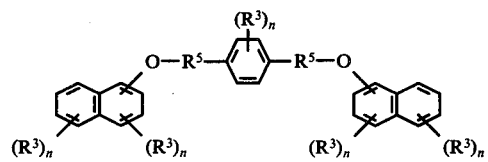
(IX)

or

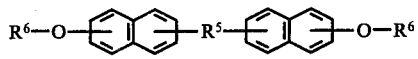

wherein the individual radical $R^3$ may be identical or different and each is alkyl or alkoxy in each case of one to four carbon atoms cycloalkyl or cycloalkoxy of five or six carbon atoms, hydrogen or $-(OR^5)_n-CH_3$, $R^4$ is alkylene of two to four carbon atoms or

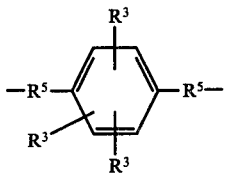

in which $R^3$ has the above meanings, $R^5$ is alkylene of two to four carbon atoms, $R^6$ is alkyl of one to four carbon aoms and $n$ is zero, 1, 2 or 3 and the said radicals may bear groups which are inert under the reaction conditions for example alkoxy or alkyl of one to three carbon atoms in each case as substituents, reacting the sodium naphtholate from said first stage with carbon dioxide in a second stage at a temperature of at least 180° C, and acidifying the sodium salts of 2-hydroxynaphthalene-3-carboxylic acid to convert it to 2-hydroxynaphthalene-3-carboxylic acid.

11. A process as set forth in claim 10 wherein the amount of the aromatic ether employed is in the range of 20 to 100% by weight based on said naphtholate.

12. A process as set forth in claim 10 wherein the carboxylation in the second stage is conducted at a pressure in the range of from 2 to 50 atmospheres and with an amount of carbon dioxide in the range of from 0.5 mole to 10 moles, based on said naphtholate.

13. A process as set forth in claim 10 wherein said aromatic ether is 1,2-dinaphthoxyethane.

14. A process for the production of 2-hydroxynaphthalene-3-carboxylic acid which comprises heating sodium β-naphtholate in a first stage to a temperature of at least 180° C as a solution or suspension in an aromatic ether having one of the formulae

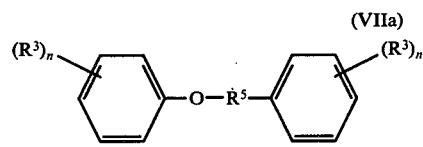
(VIIa)

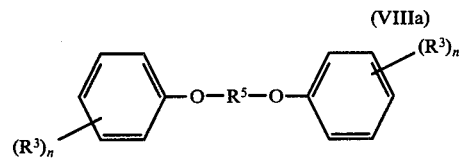
(VIIIa)

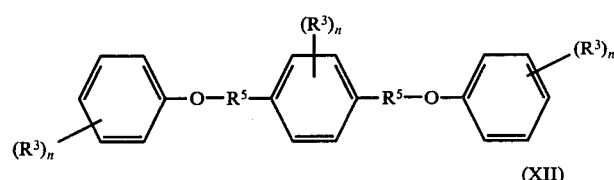
(XII)

or

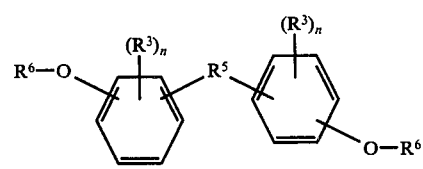
(XIII)

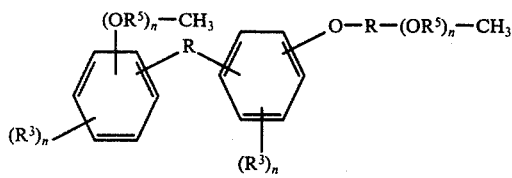

wherein the individual radical R³ may be identical or different and each is alkyl or alkoxy in each case of one to four carbon atoms, cycloalkyl or cycloalkoxy of five or six carbon atoms, hydrogen or —(OR⁵)ₙ—CH₃, R⁴ is alkylene of two to four carbon atoms or

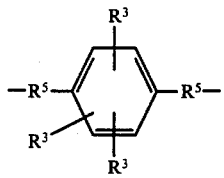

in which R³ has the above meanings, R⁵ is alkylene of two to four carbon atoms, R⁶ is alkyl of one to four carbon atoms and n is zero, 1, 2 or 3 and the said radicals may bear groups which are inert under the reaction conditions for example alkoxy or alkyl of one to three carbon atoms in each case as substituents, reacting the sodium naphtholate from said first stage with carbon dioxide in a second stage at a temperature of at least 180° C, and acidifying the sodium salts of 2-hydroxynaphthalene-3-carboxylic acid to convert it to 2-hydroxynaphthalene-3-carboxylic acid.

15. A process as set forth in claim 14 wherein the amount of the aromatic ether employed is in the range of 20 to 100% by weight based on said naphtholate.

16. A process as set forth in claim 14 wherein the carboxylation in the second stage is conducted at a pressure in the range of from 2 to 50 atmospheres and with an amount of carbon dioxide in the range of from 0.5 mole to 10 moles, based on said naphtholate.

17. A process as set forth in claim 14 wherein said aromatic ether is 1,4-diphenoxybutane, 1,2-diphenoxyethane, 1,2-dio-(3'-methyl)-phenoxyethane, or 4,4'-dimethoxydiphenylethane.

18. A process as set forth in claim 14 wherein said aromatic ether is ω,ω'-diphenoxy-1,4-diethylenebenzene.

* * * * *

UNITED STATES PATENT AND TRADEMARK OFFICE
CERTIFICATE OF CORRECTION

PATENT NO. : 4,038,309
DATED : July 26, 1977
INVENTOR(S) : Hoch et al

It is certified that error appears in the above-identified patent and that said Letters Patent are hereby corrected as shown below:

In column 13, under Claim 1, line 4:

"a solution of suspension" should be corrected to read --a solution or suspension--.

In column 14, line 2 after the formulas:

"cyclonexyl" should be corrected to read

--cyclohexyl--.

In column 18, under Claim 17, line 3:

"dio-(3'...)" should be corrected to read

--di-(3'...)--.

Signed and Sealed this

Twenty-fifth Day of July 1978

[SEAL]

Attest:

RUTH C. MASON
Attesting Officer

DONALD W. BANNER
Commissioner of Patents and Trademarks